(12) United States Patent
Tran et al.

(10) Patent No.: US 9,861,815 B2
(45) Date of Patent: Jan. 9, 2018

(54) INTERVENTIONAL MEDICAL SYSTEMS, TOOLS, AND SUBASSEMBLIES

(71) Applicant: Medtronic, Inc., Minneapolis, MN (US)

(72) Inventors: Don H Tran, Novato, CA (US); Brent L Locsin, San Francisco, CA (US); William A Berthiaume, Santa Rosa, CA (US); Maria E Valdovinos, Santa Rosa, CA (US); H. Allan Steingisser, Santa Rosa, CA (US); Erik Griswold, Penngrove, CA (US)

(73) Assignee: Medtronic, Inc., Minneapolis, MN (US)

( * ) Notice: Subject to any disclaimer, the term of this patent is extended or adjusted under 35 U.S.C. 154(b) by 367 days.

(21) Appl. No.: 14/231,976

(22) Filed: Apr. 1, 2014

(65) Prior Publication Data

US 2015/0273207 A1 Oct. 1, 2015

(51) Int. Cl.
*A61N 1/05* (2006.01)
*A61N 1/372* (2006.01)
*A61N 1/375* (2006.01)
*A61B 90/00* (2016.01)

(52) U.S. Cl.
CPC .......... *A61N 1/059* (2013.01); *A61N 1/372* (2013.01); *A61B 2090/064* (2016.02); *A61B 2090/0807* (2016.02); *A61N 1/057* (2013.01); *A61N 1/3756* (2013.01); *A61N 1/37205* (2013.01); *A61N 2001/0578* (2013.01)

(58) Field of Classification Search
CPC ................ A61N 1/3756; A61N 1/3622; A61N 2001/0578; A61N 1/37205

USPC ......................................................... 607/126
See application file for complete search history.

(56) References Cited

U.S. PATENT DOCUMENTS 5,441,055 A * 8/1995 Ales ................. A61M 25/0905
600/434
2012/0172690 A1 7/2012 Anderson et al.
2012/0172891 A1 7/2012 Lee
(Continued)

FOREIGN PATENT DOCUMENTS

WO 2012092074 A1 7/2012

OTHER PUBLICATIONS (PCT/US2015/023278) PCT Notification of Transmittal of the International Search Report and the Written Opinion of the International Searching Authority, dated Jul. 10, 2015, 10 pages.

*Primary Examiner* — Alyssa M Alter

(57) ABSTRACT

A tether subassembly, which may be employed by a tool that deploys an implantable medical device, includes a test segment for verification of adequate fixation of the device at an implant site. When the device is located in proximity to a distal opening of the tube, a tether first length extends through an attachment structure of the device and within an elongate tube of the tool, a tether second length extends alongside the tether first length within the tube, and the test segment is located in proximity to the distal opening. The test segment is configured so that only a tug force, applied to the tether first length, and greater than or equal to a predetermined force, can pull the test segment through an aperture, either of the delivery tool or of the device. The predetermined force corresponds to a minimum adequate fixation force for the device.

23 Claims, 6 Drawing Sheets

(56) References Cited

U.S. PATENT DOCUMENTS

2013/0053921 A1    2/2013  Bonner et al.
2013/0079861 A1    3/2013  Reinert et al.
2013/0103047 A1*   4/2013  Steingisser .......... A61N 1/3756
                                                        606/129

* cited by examiner

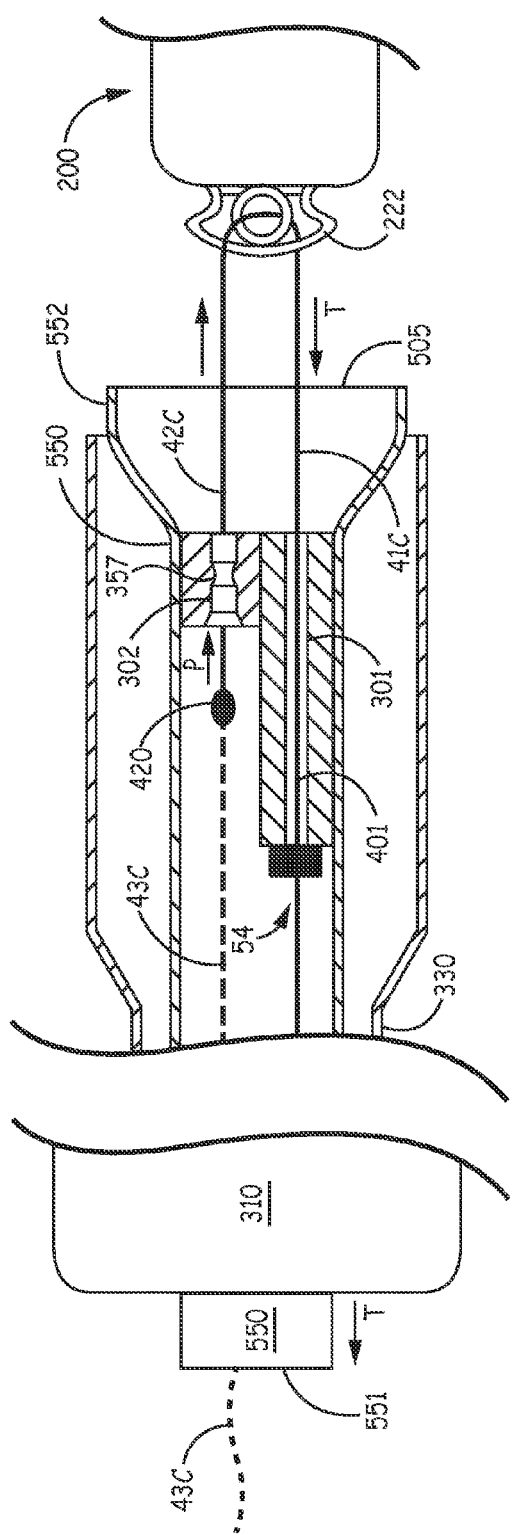
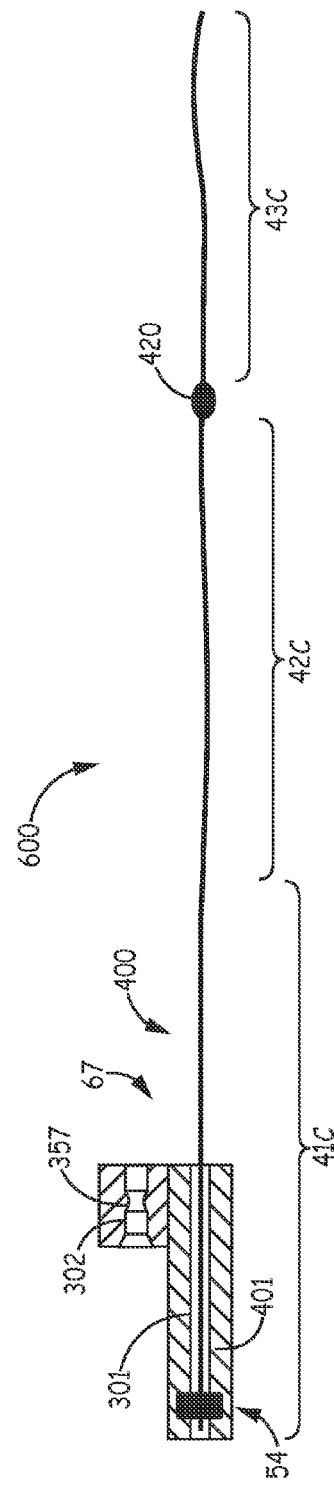
FIG. 5A
FIG. 5B

INTERVENTIONAL MEDICAL SYSTEMS, TOOLS, AND SUBASSEMBLIES

FIELD OF THE DISCLOSURE

The present invention pertains to interventional medical systems, and more particularly to tools and subassemblies thereof that facilitate percutaneous transvenous deployment and fixation verification of relatively compact implantable medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode that is positioned at a pacing site, either endocardial or epicardial. Mechanical complications and/or MRI compatibility issues, which are sometimes associated with elongate lead wires, have motivated the development of implantable cardiac pacing devices that are wholly contained within a relatively compact package for implant in close proximity to the pacing site, for example, within the right ventricle RV of the heart. With reference to FIGS. 1A-B, such a device 200 is illustrated, wherein an hermetically sealed housing 205, preferably formed from a biocompatible and biostable metal such as titanium, contains a pulse generator, or an electronic controller (not shown), to which at least one electrode 211 is coupled, for example, by a hermetic feedthrough assembly (not shown) known to those skilled in the art of implantable medical devices. Housing 205 may be overlaid with an insulative layer, for example, medical grade polyurethane, parylene, or silicone.

FIG. 1A illustrates device 200 implanted at a target site 150 in the apex of the right ventricle RV, for example, being fixed in place by a fixation member 215 that includes a plurality of tines, which are better seen in FIG. 1B. Embodiments of the illustrated fixation member 215 are described in commonly assigned U.S. Patent application 2012/0172690, which is hereby incorporated by reference in its entirety. FIG. 1A further illustrates device 200 having been deployed out from a distal portion of an elongate delivery tool 100, for example, a guiding catheter, which has been maneuvered up through the inferior vena cava IVC and into the right ventricle RV from the right atrium RA, according to methods known in the art of interventional cardiology.

FIGS. 2A-B are plan views of a specialized tool 300 developed for the deployment of relatively compact implantable medical devices like device 200, in lieu of more common catheter-type tools, like tool 100. FIGS. 2A-B illustrate tool 300 including a handle assembly 310, an outer tube 330, and a core 350, for example, an inner elongate tube (shown with dashed lines in FIG. 2A), extending within outer tube 330. FIGS. 2A-B further illustrate outer tube 330 including a distal-most portion 332, which is sized to contain an implantable medical device, for example, the above-described device 200, which can be seen in the cut-away section of FIG. 2B, when a proximal end of the device, for example, attachment structure 222, abuts a distal member 352 of core/tube 350. Distal-most portion 332 also defines a distal opening 303 of outer tube 330, through which device 200 is deployed, for example, as shown in FIG. 2B, when outer tube 330 is withdrawn, or retracted, relative to core/tube 350, per arrow b, for example, by moving a control member 312 of handle assembly 310 per arrow B. With further reference to FIGS. 2A-B, handle assembly 310 includes another control member 311 to which a proximal end of a pull wire (not shown) may be attached; a distal end of the pull wire may be anchored adjacent to distal member 352 of core/tube 350, so that when control member 311 is moved per arrow A tool 300 is deflected per arrow a, as shown in FIG. 2B. The deflection, per arrow a, may be useful to position distal-most portion 332 in close proximity to target site 150 so that, upon retraction of outer tube 330, per arrow b, the aforementioned tines of fixation member 215 may engage with the tissue at site 150. Disclosure included in commonly assigned United States Patent Application 2013/0103047, which describes a general construction of a tool like tool 300, is hereby incorporated by reference.

With reference back to FIG. 1A a tether 140 is shown extending from an attachment structure 222 of device 200 and back into tool 100, so that a proximal portion of tether 140, which extends out from a proximal end of tool 100, is accessible to an operator. With reference to FIG. 1B, attachment structure 222 includes an eyelet 202 through which tether 140 may be looped to temporarily secure device 200 to tether 140. Tether 140 may similarly be secured to device 200, when device 200 is loaded in tool 300 for deployment. With reference to FIGS. 2A-B, the looped tether 140 extends within core/tube 350 so that ends of tether 140 extend from a proximal opening 351 of core 350, where the operator may tug on tether 140 to test the fixation of device 200 at the implant site, and, if necessary, apply a greater force to tether 140 to remove device 200 from the implant site for repositioning at a more suitable site. If the operator is satisfied with the performance of device 200 at the illustrated implant site, the operator may release tether 140 from attachment structure 222 and withdraw tether 140 through delivery tool 300.

SUMMARY

Because an operator performing a simple tug test, for example, as described above, does not necessarily know how much force to apply to verify adequate fixation of an implanted device, and because, from operator to operator, the applied tug force will not necessarily be the same, there is a need for the embodiments of interventional medical systems disclosed herein, which are configured to provide a calibrated tug test verification of adequate fixation for an implantable medical device at a target implant site. According to some embodiments, a delivery tool, which is configured to facilitate deployment of the implantable medical device so that a fixation member thereof engages with tissue at an implant site, employs a tether subassembly that includes a test segment for the verification of adequate fixation. When the medical device is located for deployment by the tool, in proximity to a distal opening of an elongate tube thereof, a tether first length extends through an attachment structure of the device and within the tube, a tether second length extends alongside the first length within the tube, and the test segment of the tether subassembly is located in proximity to the distal opening of the tube. The test segment is configured so that only a tug force, applied through the first length of the tether subassembly, that is greater than or equal to a predetermined force can pull the test segment of the tether subassembly through an aperture, wherein the aperture is either included in the delivery tool, for example, a channel of the elongate tube, or included in the device, for example, an eyelet of the attachment structure. The predetermined force corresponds to a minimum adequate fixation force provided by engagement of the fixation member of the device with the tissue at the implant site, so that if an operator pulls the test segment through the aperture, via the tug force, without dislodging the device, the operator can be assured that the device is adequately fixed at the implant site.

According to some embodiments, a proximal end of the first length of the aforementioned tether extends proximally from a proximal opening of the elongate tube of the delivery tool, so that the operator applies the tug force by grasping the first length of the tether in proximity to the proximal end thereof. According to some alternate embodiments, the delivery tool includes a joint that fixedly attaches the proximal end of the first length of the tether to the elongate tube of the tool, so that the operator can apply the tug force by grasping the tube.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 5A is a plan view, which includes a cross-section view, of portions of an interventional medical system, according to some additional embodiments; and FIG. 5B is a plan view, including a partial cross-section, of a tether subassembly, according to some alternate embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Furthermore, although exemplary embodiments are described in the context of interventional medical systems that provide cardiac therapy, the scope of the present invention may encompass systems suitable for other types of medical therapy.

Figure 1A:
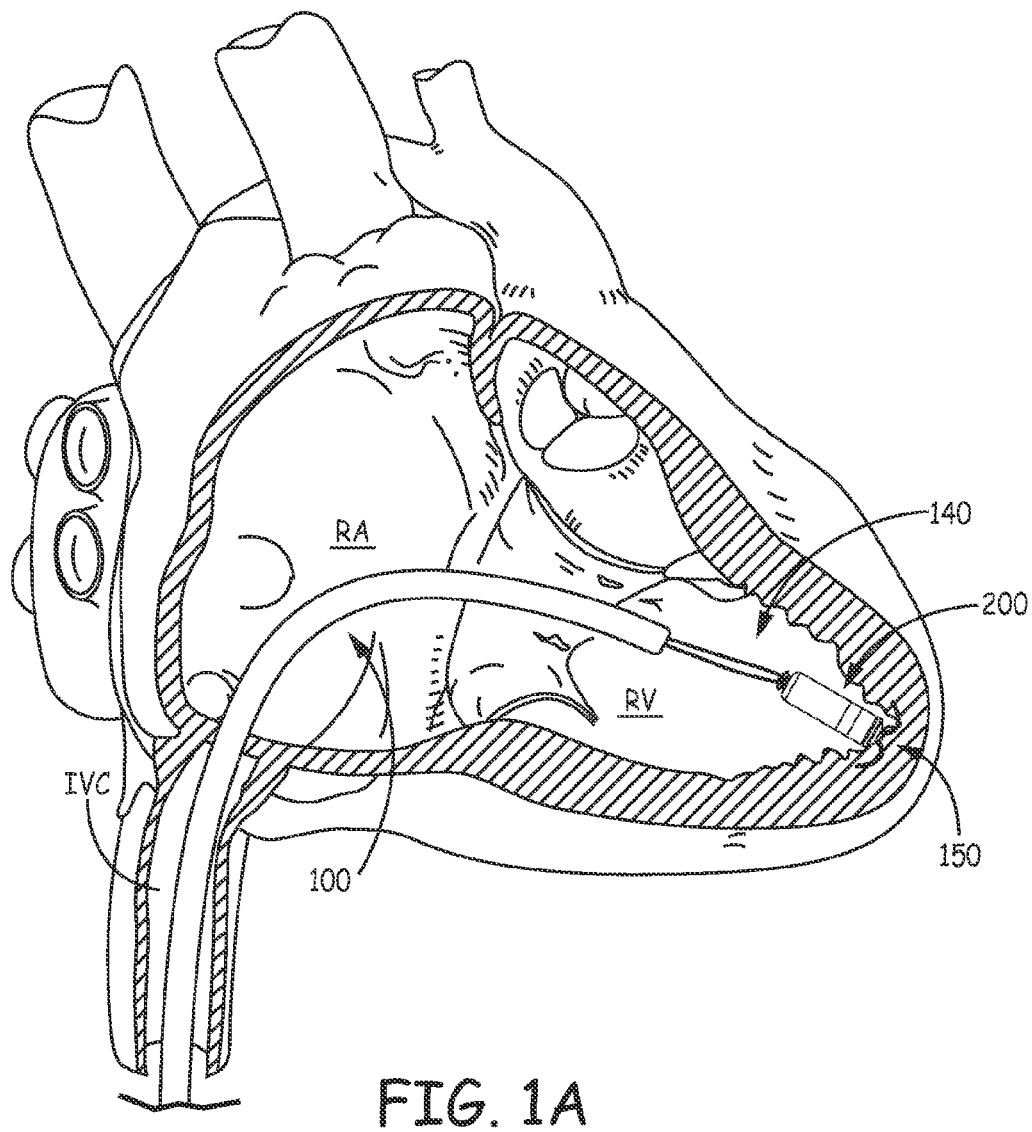
FIG. 1A is a schematic showing an implanted exemplary implantable medical device.
Figure 1B:
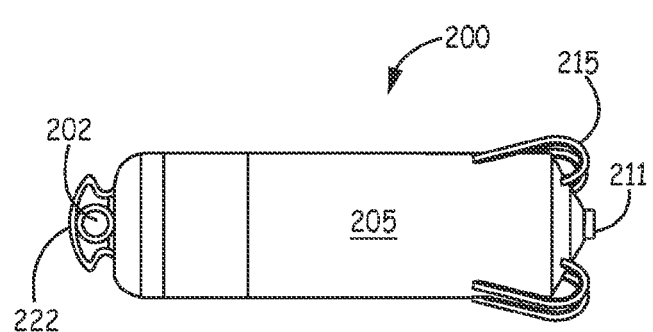
FIG. 1B is a plan view of the exemplary medical device.
Figure 2A:
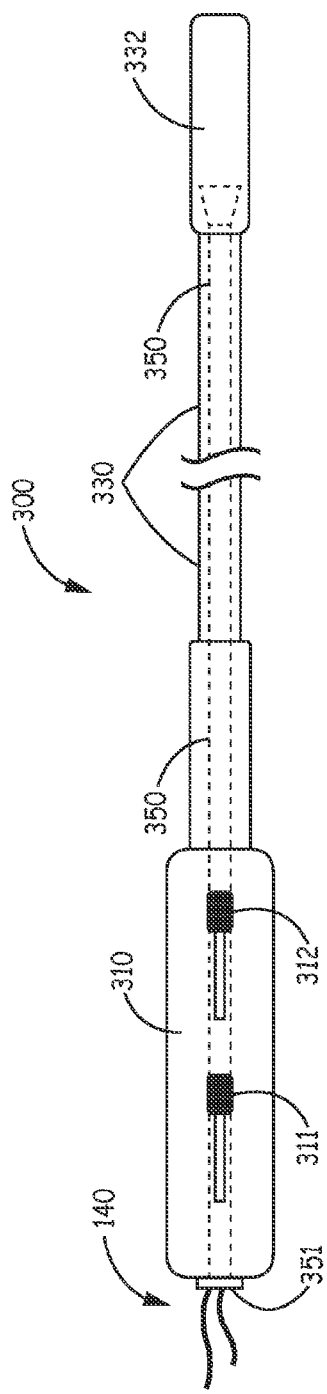
FIG. 2A is a plan view of an exemplary delivery tool.
Figure 2B:
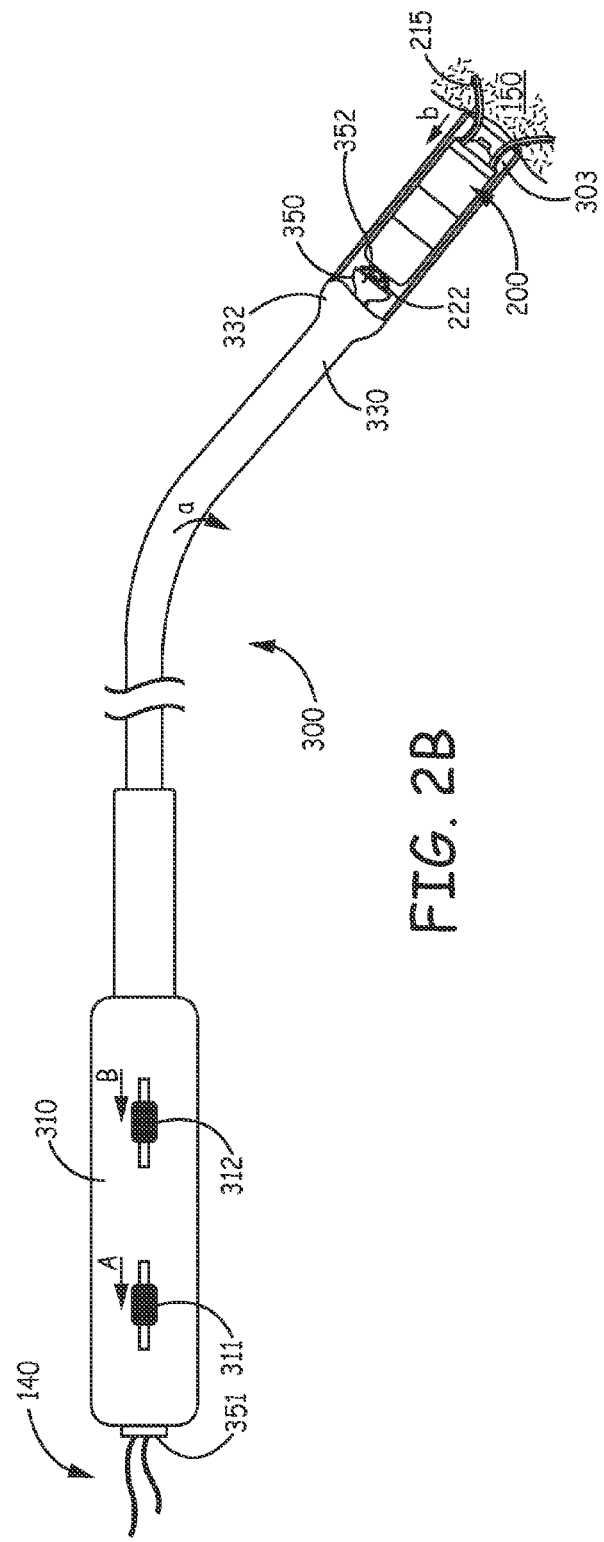
FIG. 2B is a plan view of an exemplary interventional medical system including the tool of FIG. 2A and the device of FIG. 1B.
Figure 3A:
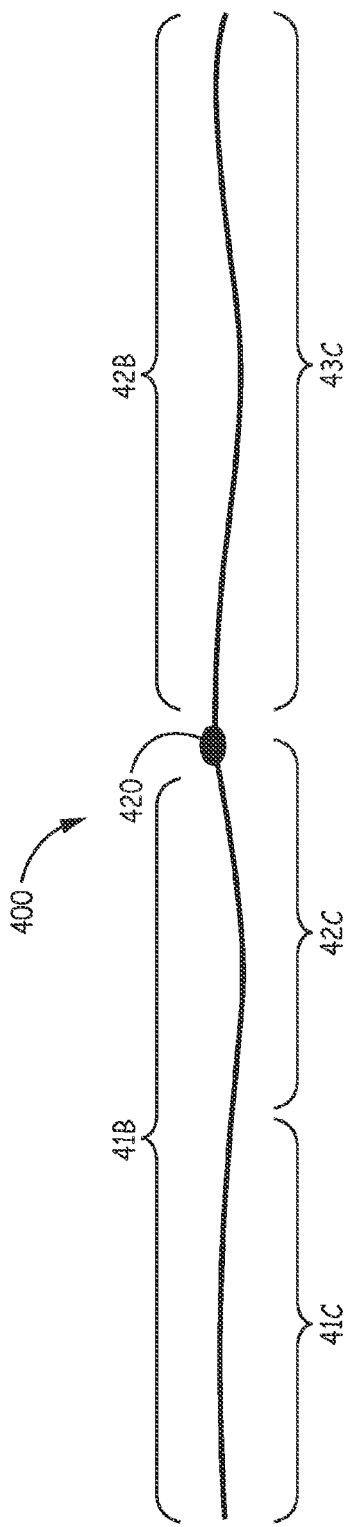
FIG. 3A is a plan view of a tether subassembly, according to some embodiments of the present invention.
Figure 3B:
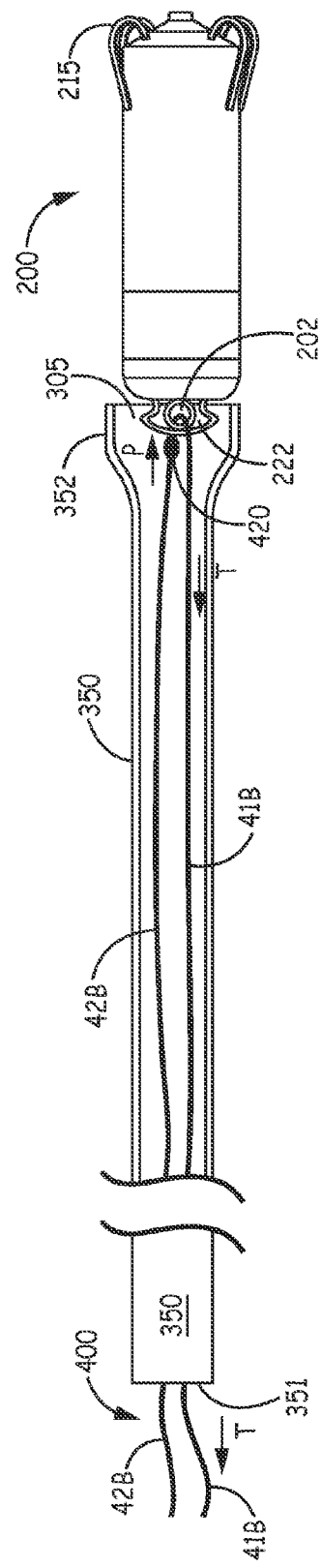
FIG. 3B is a plan view, which includes a cut-away cross-section, of a portion of the system of FIG. 2B, in which the tether subassembly of FIG. 3A is employed, according to some embodiments.

FIG. 3A is a plan view of a tether subassembly 400, according to some embodiments of the present invention; and FIG. 3B is a plan view, which includes a cut-away cross-section, of a portion of a medical interventional system, wherein tether subassembly 400 is employed in conjunction with delivery tool 300 (FIG. 2A-B), according to some embodiments. FIG. 3A illustrates tether subassembly 400 including first and second lengths 41B, 42B of one or more elongate fibers thereof, and a test segment 420 located between the first and second lengths 41B, 42B. FIG. 3B illustrates attachment structure 222 of device 200 abutting distal member 352 of tube 350, being located within a distal opening 305 thereof, and tether 400 being temporarily secured to device 200, with first length 41B of tether 400 extending through an aperture formed by eyelet 202 of attachment structure 222, and second length 42B of tether 400 extending alongside first length 41B within tube 350. Although not shown, tube 350 may be a multi-lumen tube having separate lumens to accommodate first and second lengths 41B, 42B of tether 400. FIG. 3B further illustrates proximal ends of both first and second lengths 41B, 42B of tether 400 extending out from proximal opening 351 of tube 350, and thereby accessible to an operator. First and second tether lengths 41B, 42B pass freely through the aperture formed by eyelet 202, but, according to the illustrated embodiment, test segment 420 of tether subassembly 400 is configured to be pulled through eyelet 202, per arrow P, only by a tug force, which is applied to first length 41B, for example, per arrow T, that is greater than or equal to a predetermined force, wherein the predetermined force corresponds to a minimum adequate fixation force for device 200, for example, provided by fixation member 215.

With reference back to FIG. 2B, after the operator manipulates tool 300, as described above, to deploy device 200 through distal opening 303 of outer tube 330, so that tines of fixation member 215 engage with the tissue at site 150, the operator can grasp the proximal end of tether first length 41B and perform a tug test to evaluate the fixation of the engaged tines, by applying the aforementioned tug force, per arrow T. If device 200 is not adequately fixed at site 150, the applied tug force will dislodge the engagement of fixation member 215 without pulling test segment 420 through eyelet 202 of device attachment structure 222; but, if the tug force pulls test segment 420 of tether subassembly 400 through eyelet 202, without dislodging fixation member 215, the operator can be assured that device 200 is adequately fixed at site 150. According to some embodiments, an interference fit of test segment 420 within eyelet 202, for example, approximately 0.001 inch interference, assures that the applied tug force will only pull test segment 420 through eyelet 202 when device 200 is adequately fixed at site 150. An adequate fixation force for device 200 may be approximately 1.5 Newtons.

Any suitable biocompatible fiber, for example, a polyester fiber that has a fluoropolymer coating, such as PTFE, may form first and second lengths 41B, 42B of tether 400, and test segment 420 may be formed from a biocompatible polymer material such as a polyether block amide, for example, PEBAX® 3533 or 4033, silicone, or polyurethane. According to some exemplary embodiments, test segment 420 is positioned around a single elongate fiber of tether subassembly 400 and is fixedly coupled thereto at a location that segregates first and second lengths 41B, 42B of tether subassembly 400. For example, test segment 420 may be insert-molded around the fiber, or test segment 420 may be formed with a through-hole, through which the fiber of tether 400 is threaded and subsequently bonded therein, for example, with any suitable biocompatible adhesive known in the art. The material forming test segment 420, for example, polyurethane or one of the aforementioned PEBAX® materials, may be blended with another material, for example, 10% Siloxane, to make an external surface of test segment 420 more lubricious. According to some embodiments, test segment 420 is radiopaque so that the operator may monitor, via fluoroscopy, the position of test segment 420 relative to the aperture of the system, for example, eyelet 202 of device attachment structure 222, which is also, preferably radiopaque. Thus, the material forming test segment 420, for example, either the aforementioned PEBAX® materials, may be blended with a radiopaque material, for example, 40% Barium Sulfate (BaSO4) or Bismuth Subcarbonate. If test segment 420 is not radiopaque, the operator may rely on a slackening, or reduction in tension, of tether first length 41B, during the tug test, as an indication that the tug force has pulled test segment 420 through eyelet 202.

Figure 3C:
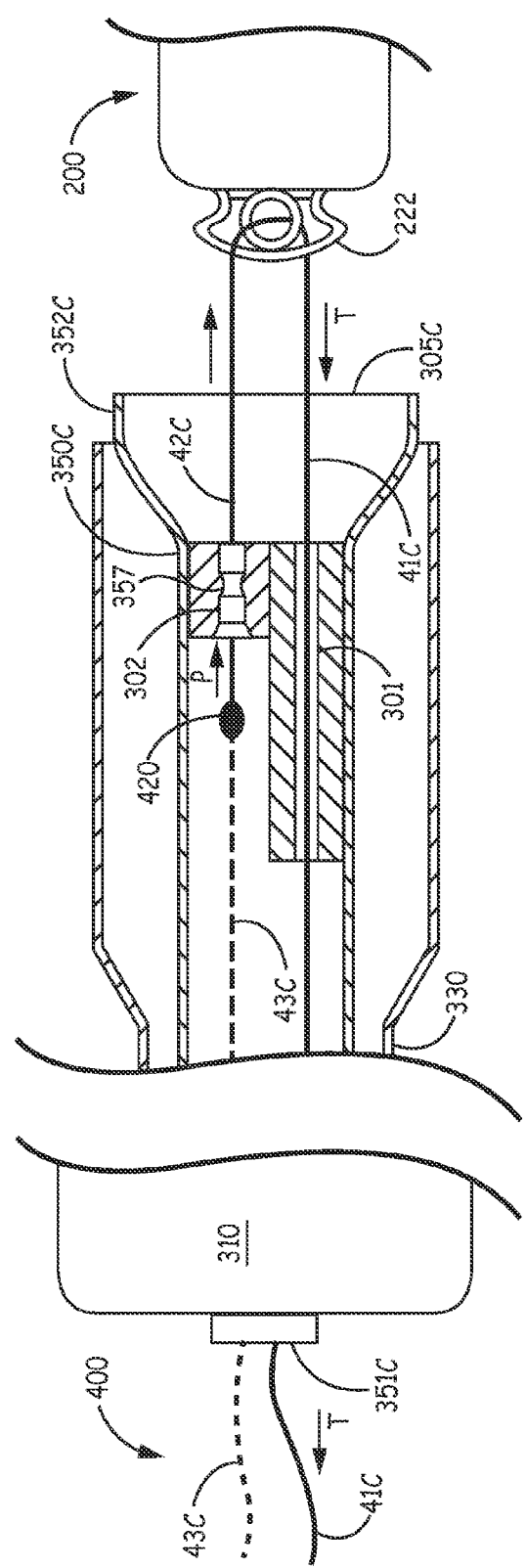
FIG. 3C is a plan view, which includes a cross-section view, of portions of an interventional medical system, according to some alternate embodiments.

With further reference to FIG. 3A, in conjunction with FIG. 3C, tether subassembly 400 may alternately be employed in conjunction with an alternate embodiment of tool 300. FIG. 3C is a plan view of proximal and distal portions of an interventional system, with a cross-section view through a distal end of the delivery tool thereof. The illustrated delivery tool differs from the above described tool 300, in that a core/elongate tube 350C, which extends within outer tube 330 in lieu of tube 350, includes a channel 357 located in proximity to a distal opening 305C thereof, wherein a distal member 352C of tube 350C may define distal opening 305C. According to the illustrated embodiment, channel 357 forms an aperture of the system through which test segment 420 of tether subassembly 400 can only be pulled by a tug force, per arrow T, that is greater than or equal to the above-described predetermined force. According to some embodiments, an interference fit of test segment 420 within channel 357, for example, approximately 0.001 inch interference, assures that the applied tug force will only pull test segment 420 through channel 357 when device 200 is adequately fixed at an implant site. FIGS. 3A and 3C illustrate tether subassembly 400 including first and second lengths 41C, 42C, wherein second length 42C extends between first length 41C and test segment 420. Tether first and second lengths 41C, 42C extend alongside one another within tube 350C, when tether 400 is temporarily secured through attachment structure 222 of device 200, and when test segment 420 is positioned proximal to channel 357, as shown, to temporarily attach device 200 to the delivery tool. According to the illustrated embodiment, tube 350C is a multi-lumen tube, which has a first lumen 301, through which at least first and second lengths 41C, 42C may freely pass, and a second lumen 302, in which a constricted portion forms channel 357. FIG. 3C further illustrates a proximal end of tether first length 41C extending out from a proximal opening 351C of tube 350C, in proximity to handle assembly 310, so that an operator may apply the tug force, per arrow T, thereto.

Figure 4:
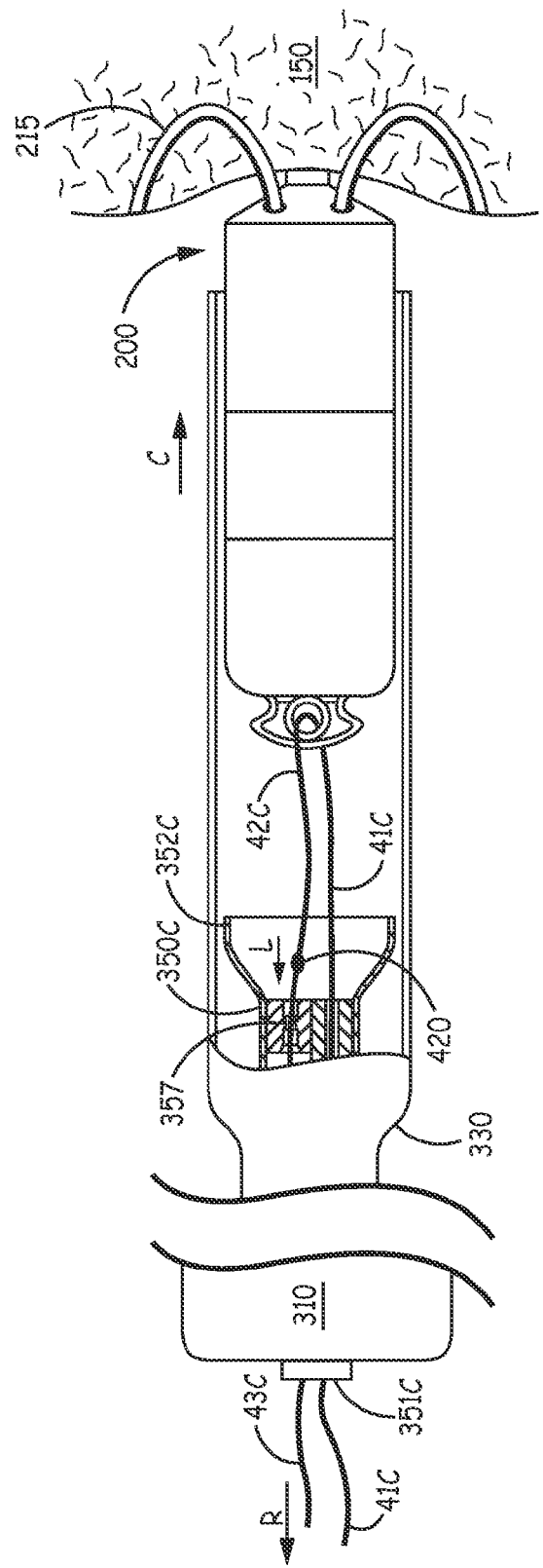
FIG. 4 is another plan view of the system of FIG. 3C, according to some embodiments.

According to some embodiments, tether subassembly 400, as employed within tube 350C, may further include a third length 43C (shown with dashed lines in FIG. 3C) that extends proximally from test segment 420 and out through proximal opening 351C of tube 350C. Alternately, the optional third length 43C may be relatively short such that third length 43C only extends within the illustrated distal portion of the tool. However, the optional third length 43C may be long enough so that third length 43C is accessible to the operator, in proximity to proximal opening 351C, even after a tug test is performed that pulls test segment 420 through channel 357, for example, as shown in FIG. 4, to verify adequate fixation of device 200. With reference to FIG. 4, a force, per arrow R, may be applied to tether third length 43C to then pull tether test segment 420 back through channel 357 of inner tube 350C, per arrow L, thereby re-creating the temporary attachment between device 200 and the delivery tool, which is illustrated in FIG. 3C. After re-creating the temporary attachment, device 200 may be extracted from implant site 150 for repositioning at another implant site, for example, by pulling on both of tether first and third lengths 41C, 43C, with a force sufficient to disengage device fixation member 215, and then advancing outer tube 330 of the tool, per arrow C, back over device 200, for example by moving control member 312 of handle assembly 310 in an opposite direction to that designated by arrow B in FIG. 2B.

First and second lengths 41C, 42C, and optional third length 43C of tether 400, as employed in the tool of FIGS. 3C and 4, may be formed any suitable biocompatible fiber, as described above, wherein test segment 420 is likewise formed according to any of the above-described embodiments. Lumen 302 and channel 357 of tube 350C may be formed by an insert member, for example, which is formed from a biocompatible polymer material, such as PEBAX® 3533 or 4033, silicone, or polyurethane, and fixedly attached to a wall of tube 350C, and wherein a remainder of tube 350C may be formed from a similar material. The insert member, which may also include first lumen 301, may be molded separately and then bonded to the wall of tube 350C (e.g., via thermal bonding or adhesive bonding according to methods known in the art). Alternately, the insert member may be insert-molded together with the wall of tube 350C. If test segment 420 of tether subassembly 400 is radiopaque, and if channel 357 of the insert member is also formed from a radiopaque material (e.g., similar to that described above for test segment 420), the operator may monitor a position of test segment 420 relative to channel 357, via fluoroscopy. Alternately, if channel 357 is not radiopaque, distal member 352C of tube 350C may be radiopaque, so that the operator may monitor the position of a radiopaque test segment 420 relative to distal member 352C. Thus, when the operator sees, via fluoroscopy, radiopaque test segment 420 merging with the radiopaque distal member 352C during the tug test, the operator may be assured that the tug force has pulled test segment 420 through channel 357, which is located proximal to distal member 352C. According to an exemplary embodiment, distal member 352C is formed from a radiopaque material, such as PEBAX® 7033 blended with BaSO4, separate from a remainder of tube 350C before being bonded thereto. If none of test segment 420, channel 357 and distal member 352C is radiopaque, the operator may rely on a slackening, or reduction in tension, of tether first length 41C, during the tug test, as an indication that the tug force has pulled test segment 420 through channel 357.

FIG. 5A is a plan view of proximal and distal portions of another embodiment of an interventional system, with a cross-section view through a distal end of the delivery tool thereof. The illustrated delivery tool includes an elongate tube 550 extending within outer tube 330; and tube 550, like tube 350C shown in FIG. 3C, includes channel 357 located in proximity to a distal opening 505 of tube 550. First and second tether lengths 41C, 42C also extend alongside one another in tube 550 when test segment 420 is located proximal to channel 357 to temporarily attach device 200 to the delivery tool. But, the tool of FIG. 5A differs from that shown in FIG. 3C, in that tube 550 includes a joint 54, for example, formed by an adhesive bond and/or by an interlocking fit, which fixedly attaches a proximal end 401 of tether first length 41C to tube 550. Thus, rather than applying the above-described tug force, per arrow T, directly to tether first length 41C, the operator applies the tug force to tube 550, for example, by grasping and pulling on handle assembly 310, to which tube 550 is fixedly attached, or by grasping and pulling directly on a proximal portion of tube 550 in proximity to handle assembly 310. According to some embodiments, tube 550 includes a distal member 552 that defines distal opening 505, and test segment 420 and distal member 552 are radiopaque. Thus, as described above for the tool of FIG. 3C, the operator may monitor, via fluoroscopy, the position of test segment 420 relative to distal member 552, during the tug test, and, when the operator sees radiopaque test segment 420 merging with the radiopaque distal member 552, the operator may be assured that the tug force has pulled test segment 420 through channel 357, which is located proximal to distal member 552. FIG. 5A further illustrates the optional tether third length 43C extending proximally from test segment 420 and out from a proximal opening 551 of tube 550, wherein third length 43C may be employed in a fashion similar to that described above in conjunction with FIG. 4.

With further reference to FIG. 5A, in conjunction with FIG. 5B, first and second lumens 301, 302 of tube 505, including channel 357, may be formed by an insert member similar to that described above in conjunction with FIG. 3C. FIG. 5B shows such an insert member 67, which is joined together with tether subassembly 400 to form another tether subassembly 600, according to some alternate embodiments, wherein after joining tether first length 41C to insert member 67, insert member 67 can be fixedly attached to a wall of tube 550, for example, via thermal bonding or adhesive bonding according to methods known in the art. According to some embodiments, a surface of lumen 301 is fixedly adhered to proximal end 401 of tether first length 41C to form the aforementioned joint 54, for example, by adhesive bonding and/or insert-molding. Alternately, or in addition, joint 54 includes a mechanical interlock between proximal end 401 of tether first length 41C and first lumen 301 of insert member 67, for example, as illustrated in FIG. 5B.

In the foregoing detailed description, the invention has been described with reference to specific embodiments. However, it may be appreciated that various modifications and changes can be made without departing from the scope of the invention as set forth in the appended claims.

The invention claimed is:

1. An interventional medical system comprising an implantable device and a delivery tool facilitating deployment of the implantable device, the device including an attachment structure and a fixation member, the fixation member being configured to engage tissue at an implant site; and the delivery tool comprising:
   an elongate tube extending from a proximal opening thereof to a distal opening thereof; and
   a tether subassembly including a first length, a second length, and a test segment, the first length extending within the elongate tube and through the attachment structure of the device, when the device is located in proximity to the distal opening of the tube, the second length extending alongside the first length within the tube, the first and second lengths each being configured to pass freely through an aperture of the system, the test segment being located in proximity to the distal opening of the tube, and the test segment being configured to be pulled through the aperture of the system only by a tug force that is greater than or equal to a predetermined force, the tug force being applied to the first length of the tether subassembly, and the predetermined force corresponding to a minimum adequate fixation force provided by engagement of the fixation member with the tissue at the implant site; and
   wherein the aperture of the system comprises one of: an eyelet of the attachment structure of the device, through which the first length of the tether subassembly extends, and a channel located within the elongate tube of the tool in proximity to the distal opening of the tube.

2. The system of claim 1, wherein a proximal end of the first length of the tether subassembly extends proximally out from the proximal opening of the elongate tube of the delivery tool.

3. The system of claim 1, wherein the delivery tool further comprises a joint fixedly attaching a proximal end of the first length of the tether subassembly to the elongate tube.

4. The system of claim 1, wherein:
   the second length of the tether subassembly of the delivery tool extends between the first length of the tether subassembly and the test segment of the tether subassembly; and
   the aperture of the system comprises the channel of the elongate tube of the tool.

5. The system of claim 4, wherein a proximal end of the first length of the tether subassembly extends proximally out from the proximal opening of the elongate tube.

6. The system of claim 4, wherein the delivery tool further comprises a joint fixedly attaching a proximal end of the first length of the tether subassembly to the elongate tube.

7. The system of claim 4, wherein the tether subassembly of the delivery tool further includes a third length extending from the test segment of the tether subassembly, through the elongate tube of the tool, and out from the proximal opening of the tube.

8. The system of claim 4, wherein the elongate tube of the delivery tool is a multi-lumen tube, the first length of the tether subassembly of the tool extending within a first lumen of the tube, the second length of the tether subassembly extending within a second lumen of the tube, and the channel being located within the second lumen.

9. The system of claim 4, wherein the delivery tool further comprises an insert member attached to a wall of the elongate tube, the insert member including the channel formed therein.

10. The system of claim 4, wherein:
    the elongate tube of the delivery tool further includes a distal member defining the distal opening thereof, the distal member being radiopaque, and the channel of the tube being located proximal to the distal member and not radiopaque; and
    the test segment of the tether subassembly of the delivery tool is radiopaque.

11. The system of claim 1, wherein:
    the test segment of the tether subassembly of the delivery tool is located between the first length of the tether subassembly and the second length of the tether subassembly; and
    the aperture of the system comprises the eyelet of the attachment structure of the medical device.

12. The system of claim 1, wherein the test segment of the tether subassembly of the delivery tool is radiopaque.

13. A delivery tool facilitating deployment of an implantable medical device, the device including an attachment structure and a fixation member, the fixation member being configured to engage tissue at an implant site, and the delivery tool comprising:

an elongate tube extending from a proximal opening thereof to a distal opening thereof, and the tube further including a channel located in proximity to the distal opening; and a tether subassembly including a first length, a second length, and a test segment, the first length extending within the elongate tube and out through the distal opening of the tube, the first length being configured to freely pass through the attachment structure of the device, the second length extending from the first length, back through the distal opening of the elongate tube, and through the channel of the tube, when the first length passes through the attachment structure of the device, and the test segment terminating the second length, the test segment being configured to be pulled through the channel, toward the distal opening, only by a tug force that is greater than or equal to a predetermined force, the tug force being applied to the first length of the tether subassembly, and the predetermined force corresponding to a minimum adequate fixation force provided by engagement of the fixation member with the tissue at the implant site.

14. The tool of claim 13, wherein a proximal end of the first length of the tether subassembly extends proximally out from the proximal opening of the elongate tube.

15. The tool of claim 13, further comprising a joint fixedly attaching a proximal end of the first length of the tether subassembly to the elongate tube.

16. The tool of claim 13, wherein the elongate tube is a multi-lumen tube, the first length of the tether subassembly extending within a first lumen of the tube, the second length of the tether subassembly extending within a second lumen of the tube, and the channel being located within the second lumen.

17. The tool of claim 13, further comprising an insert member attached to a wall of the elongate tube, the insert member including the channel formed therein.

18. The tool of claim 17, wherein:

the elongate tube further includes a distal member defining the distal opening thereof, the distal member being radiopaque, and the channel being located proximal to the distal member and not radiopaque; and the test segment of the tether subassembly is radiopaque.

19. The tool of claim 13, wherein the tether subassembly further includes a third length extending from the test segment, through the elongate tube of the tool and proximally out from the proximal opening of the elongate tube.

20. The tool of claim 13, wherein the test segment of the tether subassembly is radiopaque.

21. A tether subassembly for an interventional medical system, the tether subassembly comprising an elongate fiber and a test segment fixedly coupled to the fiber, the fiber configured to freely pass through an aperture of the system, and the test segment forming an interference fit with the aperture such that only a tug force, which is applied to a length of the fiber, and which is greater than or equal to a predetermined force, can pull the test segment through the aperture.

22. The tether subassembly of claim 21, wherein the test segment is radiopaque.

23. The tether subassembly of claim 21, further comprising an insert member fixedly attached to a proximal end of the length of the fiber, the insert member including the aperture of the system formed therein, and the insert member being configured for attachment to a wall of an elongate tube of a delivery tool of the system.

* * * * *